(12) United States Patent
Hughes

(10) Patent No.: US 8,741,149 B2
(45) Date of Patent: Jun. 3, 2014

(54) MASS SPECTROMETER

(75) Inventor: Christopher Hughes, Manchester (GB)

(73) Assignee: Micromass UK Limited, Wilmslow (GB)

( * ) Notice: Subject to any disclaimer, the term of this patent is extended or adjusted under 35 U.S.C. 154(b) by 1348 days.

(21) Appl. No.: 12/056,762

(22) Filed: Mar. 27, 2008

(65) Prior Publication Data

US 2009/0166525 A1    Jul. 2, 2009

Related U.S. Application Data

(63) Continuation of application No. 11/051,582, filed on Feb. 4, 2005, now abandoned.

(60) Provisional application No. 60/543,889, filed on Feb. 12, 2004.

(51) Int. Cl.
*G01N 30/32* (2006.01)
*G01N 30/10* (2006.01)
*G01N 30/72* (2006.01)
*B01D 15/16* (2006.01)

(52) U.S. Cl.
CPC ............... *G01N 30/32* (2013.01); *G01N 30/10* (2013.01); *G01N 30/7233* (2013.01); *B01D 15/163* (2013.01)
USPC ...................................... 210/656; 210/198.2

(58) Field of Classification Search
CPC ....... G01N 30/02; G01N 30/10; G01N 30/32; G01N 30/7233; B01D 15/163
USPC ............... 210/635, 656, 659, 198.2; 436/161; 422/70
See application file for complete search history.

(56) References Cited

U.S. PATENT DOCUMENTS

| | | | |
|---|---|---|---|
| 4,070,284 A | 1/1978 | Fujita et al. | |
| 4,116,046 A | 9/1978 | Stein | |
| 4,239,623 A | 12/1980 | Schrenker | |
| 4,364,263 A | 12/1982 | Sankoorikal et al. | |
| 4,437,812 A | 3/1984 | Abu-Shumays et al. | |
| 4,534,207 A | 8/1985 | Szakasits et al. | |
| 4,595,495 A | 6/1986 | Yotam et al. | |
| 4,595,496 A | 6/1986 | Carson | |
| 6,139,734 A | 10/2000 | Settlage et al. | |
| 6,402,946 B1 | 6/2002 | Spraul et al. | |
| 6,586,727 B2 | 7/2003 | Bateman et al. | |
| 6,717,130 B2 | 4/2004 | Bateman et al. | |

(Continued)

FOREIGN PATENT DOCUMENTS

| | | |
|---|---|---|
| EP | 0127908 | 12/1984 |
| EP | 1148336 | 10/2001 |

(Continued)

OTHER PUBLICATIONS

UK Patent Office, Examiner's letter with Combined Search and Examination Report, mailed Jun. 6, 2005 for Application No. GB0502366.8.

(Continued)

*Primary Examiner* — Ernest G Therkorn
(74) *Attorney, Agent, or Firm* — Diederiks & Whitelaw, PLC

(57) ABSTRACT

A method of chemical separation includes dispensing a sample from a sample pumping system, pumping a solvent from a solvent gradient pumping system to elute the dispensed sample through a separation column, identifying an analyte of interest in the eluting sample, and pumping a solvent from the sample pumping system for peak parking of the analyte in the separation column.

20 Claims, 8 Drawing Sheets

(56) References Cited

U.S. PATENT DOCUMENTS

| | | |
|---|---|---|
| 6,780,325 B1 | 8/2004 | Murata et al. |
| 2002/0072126 A1 | 6/2002 | Chervet et al. |
| 2002/0117447 A1 | 8/2002 | Wheat et al. |
| 2003/0052007 A1 | 3/2003 | Paul et al. |

FOREIGN PATENT DOCUMENTS

| | | |
|---|---|---|
| JP | 07-181173 | 7/1995 |
| JP | 2002-71657 | 3/2002 |
| WO | 02/12878 | 2/2002 |
| WO | 02/29401 | 4/2002 |
| WO | 2004/058378 | 7/2004 |

OTHER PUBLICATIONS

Snyder et al., *"Introduction to Modern Liquid Chromatography"*, John Wiley & Sons, New York, 1979, pp. 103-109, 116-117, 119-123, 181-183 and 270-280.

Compson et al., *"High Sensitivity Proteome Analysis Using a Combination of Variable Flow Chromatography and ESI-MS/MS on a Q-Tof Mass Spectrometer"*, Presented at ComBio, ASBMB Conference, Sep. 30-Oct. 4, 2001.

MASS SPECTROMETER

CROSS REFERENCE TO RELATED APPLICATIONS

This application is a continuation of U.S. application Ser. No. 11/051,582, filed Feb. 4, 2005 now abandoned, which claims priority to U.S. Provisional Patent Application Ser. No. 60/543,889, filed Feb. 12, 2004, and U.K. Patent Application Nos. 0402621.7, filed Feb., 6 2004, and 0403289.2, filed Feb. 13, 2004. The entire contents of these applications are incorporated herein by reference.

FIELD OF THE INVENTION

The present invention relates to a liquid chromatography system, a mass spectrometer, a method of liquid chromatography and a method of mass spectrometry.

BACKGROUND OF THE INVENTION

Liquid chromatography is a method by which various species from a complex mixture can be separated out into their individual components. The individual species or components will elute from the liquid chromatography system at substantially different times.

Known liquid chromatography systems include High Performance Liquid Chromatography (HPLC) systems incorporating a pumping system which comprises two solvent channels A,B. By convention solvent channel A comprises an aqueous solvent or solution (e.g. HPLC grade water with 0.1% acid) and solvent channel B comprises an organic solvent (e.g. acetonitrile or methanol with 0.1% acid). The aqueous solvent or solution A and the organic solvent B are mixed so as to provide an isocratic flow. A sample or analyte to be analysed is then introduced into the mixed solvent flow. The sample may be introduced into the mixed solvent flow either manually or by means of an auto-sampler.

The sample or analyte together with solvent mixture is then passed to an analytical column which is commonly filled with stationary phase (e.g. 5 µm silicon beads). Initially the composition of mixed solvent is set so as to comprise predominantly aqueous solvent or solution from solvent channel A. However, the proportion of organic solvent B to aqueous solvent or solution A is slowly increased in a linear manner over a period of time. Components in the liquid which are initially trapped on the analytical column will begin to become mobile again as the organic solvent gradient increases i.e. as the proportion of organic solvent B in the solvent mixture increases. For example, the relative ratio of the flow rate from the two solvent channels may be linearly varied so that, for example, the solvent mixture initially comprises ~1% organic solvent but the concentration of the solvent mixture progressively increases until the solvent mixture comprises 60% organic solvent B after a period of time of e.g. 60 minutes. As the relative composition of the mixture of the two solvents A,B is varied, different species become released from the stationary phase of the column and are subsequently detected by various means at the output to the analytical column.

The inside or internal diameters of analytical columns used in liquid chromatography applications can vary quite considerably. For example, the inside or internal diameter of an analytical column may be less than 50 µm in some applications whereas in other applications the inside or internal diameter may be in excess of 4.6 mm. The delivery flow rate required from the pumping system increases as the inside or internal diameter of the analytical column is increased and the delivery flow rate may, for example, range from several nanolitres per minute to several millilitres per minute.

It is common to use a direct flow arrangement wherein the delivery flow is passed direct to the analytical column and then on to an analytical instrument (e.g. mass spectrometer) without splitting the flow. However, there are circumstances wherein a direct flow arrangement is unsuitable.

In order to provide an accurate gradient at low flow rates (e.g. a few nanolites per minute) it is often necessary to split the delivery flow from a liquid chromatograph before the analytical instrument. There are two relatively common situations where it may, for example, be necessary to split the delivery flow. The first situation is when a large diameter HPLC analytical column is used. Conventional standard large diameter HPLC analytical columns have an internal diameter of 4.6 mm. Columns having an internal diameter of 4.6 mm are an industry standard and are reliable and robust. Such columns can also handle large quantities which can be useful in purification processes such as fraction collection. However, such large diameter columns commonly require relatively high flow rates of several millilitres per minute. Whilst it is not problematic to provide such flow rates to the analytical column, flow rates of several millilitres per minute can be too high a flow rate to be handled directly by, for example, an Electrospray Ionisation ion source which may be arranged to receive and ionise the flow eluting from the column. Relatively high flow rates may be particularly unsuitable for an Electrospray Ionisation ion source especially if the solvent mixture being used to push the sample through the analytical column contains a relatively high percentage or proportion of water. Accordingly, it then becomes necessary to split the flow either downstream from or upstream of the HPLC column so that only a proportion of the flow then passes directly to the Electrospray Ionisation ion source. The rest of the flow may be either simply dumped to waste or alternatively a specific component of interest may be collected in a vial in a process known as fraction collection.

The second situation where it may be necessary to the split the delivery flow is when using a nano-flow HPLC system. Nano-flow HPLC systems commonly utilise small internal diameter columns typically having an internal diameter <360 µm. Nano-flow HPLC systems therefore by their nature operate at relatively low flow rates typically in the range of 100 nl/min to 1000 nl/min i.e. flow rates 3-4 orders of magnitude lower than typical flow rates used with 4.6 mm internal diameter columns. A column having a small internal diameter may be used, for example, when only a very small amount of sample is available. For example, a nano-flow HPLC system may be used when analysing samples of less than 100 femtomole of a protein digest extracted from human cells. However, since HPLC pumps are relatively poor at providing an accurate, stable and reproducible solvent gradient at such relatively low flow rates, it is known to run the pumps from solvent channels A,B at relatively higher flow rates but then to split the delivery flow before the nano-flow column so that only a much lower flow rate of delivery fluid passes through and on to the nano-flow HPLC column.

Electrospray Ionisation is a commonly used technique in mass spectrometry wherein species present in a flowing solution are ionised by the application of a high voltage to an electrospray probe. Electrospray ionisation is sometimes referred to as being a soft ionisation technique since the resulting ions produced by the ion source typically comprise relatively large molecular weight species (e.g. peptides) which can then be detected as intact ions by a mass analyser.

Electrospray ionisation can be achieved at several different flow rates ranging from several nl/min (i.e. nano-flow rates) to flow rates of several ml/min.

The ion counts observed in a mass spectrometer during Electrospray ionisation are not, to a first approximation at least, flow rate dependent and therefore large sensitivity gains for the same signal to noise ratios can be achieved at lower flow rates due to much lower sample consumption.

A liquid chromatography system used in conjunction with an Electrospray Ionisation ion source mass spectrometer (LCMS) or a tandem mass spectrometer (LCMS/MS) represents a powerful analytical instrument which is widely used in many laboratories around the world. However, a limitation on the quality of data which can be achieved with low abundance species when using a liquid chromatography system coupled to a mass spectrometer is the relatively short time that any particular analyte species is actually present in the Electrospray Ionisation ion source. This also has the effect that the number of different MS/MS product ion mass spectra which can be performed and recorded is limited by the length of time that any species of parent ion is present within the ion source. This length of time is determined by the peak elution profile for the particular column being used.

It is known to attempt to effectively extend the time that a peak elutes by reducing the flow rate when species of interest are identified by a mass spectrometer. This technique is known as peak parking or variable flow chromatography. Reducing the flow rate in theory at least enables species of interest to be present in an ion source for longer periods of time without any loss of ion counts per scan.

U.S. Pat. No. 6,139,734 describes a method of variable flow chromatography wherein the flow rate is varied based upon the split ratio of different restrictors. The method described relies upon the use of two different delivery split flow ratios to determine a normal flow rate and a reduced flow rate. However, this approach suffers from the problem that the pressure equilibration is not instantaneous. Furthermore, the restrictors may become clogged causing differences in flow rate. A yet further problem with the disclosed variable flow approach is that with narrow peak elution times e.g. <0.5 min for a column having an internal diameter of 75 µm, the analyte corresponding to the eluting peak may have already completely passed through the ion source by the time that the reduced flow rate is actually fully established.

US 2002/0072126 describes another approach wherein a valve positioned post-column is switched and the species are eluted into the mass spectrometer at a low flow rate using a syringe pump. The post-column valve switches when species of interest are detected. The gradient delivery pump flow rate is halted and the column output blocked during a park event. A syringe pump then continues to elute the species into the ion source at a reduced flow rate. However, the use of a post-column valve leads to the introduction of a dead volume which is detrimental both to chromatographic performance and chromatographic resolution. The known method of using a post-column valve to enable variable flow chromatography is therefore particularly disadvantageous.

It is therefore desired to provide an improved liquid chromatography system which preferably does not suffer from some or all of the problems encountered with known liquid chromatography systems which employ variable flow rates.

SUMMARY OF THE INVENTION

According to the present invention there is provided a liquid chromatography system comprising:

a first column;

a first fluid delivery system for delivering a first fluid to the first column; and a second fluid delivery system for delivering a second different fluid to the first column;

wherein in a first mode of operation the first fluid delivery system passes the first fluid through the first column at a first flow rate; and wherein in a second mode of operation the first fluid is substantially diverted away from the first column and the second fluid delivery system passes the second different fluid through the first column at a second different flow rate.

The first column preferably comprises a reverse phase High Performance Liquid Chromatography (HPLC) column. According to a less preferred embodiment the column may comprise a normal phase column. The first column may have an internal diameter selected from the group consisting of: (i) <50 µm; (ii) 50-100 µm; (iii) 100-200 µm; (iv) 200-300 µm; (v) 300-400 µm; (vi) 400-500 µm; (vii) 500-600 µm; (viii) 600-700 µm; (ix) 700-800 µm; (x) 800-900 µm; (xi) 900-1000 µm; (xii) 1.0-1.5 mm; (xiii) 1.5-2.0 mm; (xiv) 2.0-2.5 mm; (xv) 2.5-3.0 mm; (xvi) 3.0-3.5 mm; (xvii) 3.5-4.0 mm; (xviii) 4.0-4.5 mm; (xix) 4.5-5.0 mm; (xx) 5.0-5.5 mm; (xxi) 5.5-6.0 mm; (xxii) 6.0-6.5 mm; (xxiii) 6.5-7.0 mm; (xxiv) 7.0-7.5 mm; (xxv) 7.5-8.0 mm; (xxvi) 8.0-8.5 mm; (xxvii) 8.5-9.0 mm; (xxviii) 9.0-9.5 mm; (xxix) 9.5-10.0 mm; and (xxx) > 10.0 mm.

The first column preferably has a length selected from the group consisting of: (i) <10 mm; (ii) 10-20 mm; (iii) 20-30 mm; (iv) 30-40 mm; (v) 40-50 mm; (vi) 50-60 mm; (vii) 60-70 mm; (viii) 70-80 mm; (ix) 80-90 mm; (x) 90-100 mm; (xi) 100-110 mm; (xii) 110-120 mm; (xiii) 120-130 mm; (xiv) 130-140 mm; (xv) 140-150 mm; (xvi) 150-160 mm; (xvii) 160-170 mm; (xviii) 170-180 mm; (xix) 180-190 mm; (xx) 190-200 mm; (xxi) 200-210 mm; (xxii) 210-220 mm; (xxiii) 220-230 mm; (xxiv) 230-240 mm; (xxv) 240-250 mm; (xxvi) 250-260 mm; (xxvii) 260-270 mm; (xxviii) 270-280 mm; (xxix) 280-290 mm; (xxx) 290-300 mm; and (xxxi) >300 mm.

The first column preferably comprises C4, C8 or C18 stationary phase.

The first column preferably comprises particles having a size selected from the group consisting of: (i) <1 µm; (ii) 1-2 µm; (iii) 2-3 µm; (iv) 3-4 µm; (v) 4-5 µm; (vi) 5-6 µm; (vii) 6-7 µm; (viii) 7-8 µm; (ix) 8-9 µm; (x) 9-10 µm; (xi) 10-15 µm; (xii) 15-20 µm; (xiii) 20-25 µm; (xiv) 25-30 µm; (xv) 30-35 µm; (xvi) 35-40 µm; (xvii) 40-45 µm; (xviii) 45-50 µm; (xix) >50 µm.

The first column preferably comprises particles having a pore size selected from the group consisting of: (i) <100 angstroms; (ii) 100-200 angstroms; (iii) 200-300 angstroms; (iv) 300-400 angstroms; (v) 400-500 angstroms; (vi) 500-600 angstroms; (vii) 600-700 angstroms; (viii) 700-800 angstroms; (ix) 800-900 angstroms; (x) 900-1000 angstroms; and (xi) >1000 angstroms.

The first fluid delivery system preferably comprises one, two or more than two pumps. The pumps may comprise one or more piston pumps, syringe pumps or peristaltic pumps.

The first fluid delivery system (i.e. solvent channel A) preferably includes an aqueous solvent or solution delivery device. The aqueous solvent or solution delivery device A preferably dispenses, in use, an aqueous solvent or solution A. The aqueous solvent or solution A preferably comprises HPLC grade water optionally with a small amount of acid e.g. 1% formic acid. The first fluid delivery system preferably includes an organic solvent delivery device (i.e. solvent channel B). The organic solvent delivery device B preferably dispenses, in use, an organic solvent B. The organic solvent B preferably comprises an alcohol such as methanol or propanol, or acetonitrile or tetrahydrofuran (THF).

Flows from the aqueous solvent or solution delivery device A and the organic solvent delivery device B are preferably mixed, in use, so as to preferably provide an isocratic flow of fluid (e.g. solvents A,B) to the first (analytical) column.

The second fluid delivery system preferably comprises one, two or more than two pumps. The pumps preferably comprise one or more piston pumps, syringe pumps or peristaltic pumps.

The second fluid delivery system B-C preferably comprises a sample delivery device. The second fluid delivery system C preferably provides, in use, an isocratic flow of fluid to the first column. The second fluid delivery system C preferably provides an aqueous solvent or solution which preferably comprises HPLC grade water, preferably with a small amount of acid (e.g. 1% formic acid).

The first flow rate is preferably selected from the group consisting of: (i) <10 nl/min; (ii) 10-20 nl/min; (iii) 20-30 nl/min; (iv) 30-40 nl/min; (v) 40-50 nl/min; (vi) 50-60 nl/min; (vii) 60-70 nl/min; (viii) 70-80 nl/min; (ix) 80-90 nl/min; (x) 90-100 nl/min; (xi) 100-200 nl/min; (xii) 200-300 nl/min; (xiii) 300-400 nl/min; (xiv) 400-500 nl/min; (xv) 500-600 nl/min; (xvi) 600-700 nl/min; (xvii) 700-800 nl/min; (xviii) 800-900 nl/min; (xix) 900-1000 nl/min; (xx) 1-100 nl/min; (xxi) 100-200 µl/min; (xxii) 200-300 µl/min; (xxiii) 300-400 µl/min; (xxiv) 400-500 µl/min; (xxv) 500-600 µl/min; (xxvi) 600-700 µl/min; (xxvii) 700-800 µl/min; (xxviii) 800-900 µl/min; (xxix) 900-1000 µl/min; (xxx) 1.0-2.0 ml/min; (xxxi) 2.0-3.0 ml/min; (xxxii) 3.0-4.0 ml/min; (xxxiii) 4.0-5.0 ml/min; (xxxiv) 5.0-6.0 ml/min; (xxxv) 6.0-7.0 ml/min; (xxxvi) 7.0-8.0 ml/min; (xxxvii) 8.0-9.0 ml/min; (xxxviii) 9.0-10.0 ml/min; and (xxxix) >10.0 ml/min.

The second flow rate is preferably selected from the group consisting of: (i) <10 nl/min; (ii) 10-20 nl/min; (iii) 20-30 nl/min; (iv) 30-40 nl/min; (v) 40-50 nl/min; (vi) 50-60 nl/min; (vii) 60-70 nl/min; (viii) 70-80 nl/min; (ix) 80-90 nl/min; (x) 90-100 nl/min; (xi) 100-200 nl/min; (xii) 200-300 nl/min; (xiii) 300-400 nl/min; (xiv) 400-500 nl/min; (xv) 500-600 nl/min; (xvi) 600-700 nl/min; (xvii) 700-800 nl/min; (xviii) 800-900 nl/min; (xix) 900-1000 nl/min; (xx) 1-100 µl/min; (xxi) 100-200 µl/min; (xxii) 200-300 µl/min; (xxiii) 300-400 µl/min; (xxiv) 400-500 µl/min; (xxv) 500-600 µl/min; (xxvi) 600-700 µl/min; (xxvii) 700-800 µl/min; (xxviii) 800-900 µl/min; (xxix) 900-1000 µl/min; (xxx) 1.0-2.0 ml/min; (xxxi) 2.0-3.0 ml/min; (xxxii) 3.0-4.0 ml/min; (xxxiii) 4.0-5.0 ml/min; (xxxiv) 5.0-6.0 ml/min; (xxxv) 6.0-7.0 ml/min; (xxxvi) 7.0-8.0 ml/min; (xxxvii) 8.0-9.0 ml/min; (xxxviii) 9.0-10.0 ml/min; and (xxxix) >10.0 ml/min.

The second flow rate is preferably substantially lower than the first flow rate.

The ratio of the second flow rate to the first flow rate is preferably selected from the group consisting of: (i) <1; (ii) 0.1-1; (iii) 0.01-0.1; (iv) 0.001-0.01; (v) 0.0001-0.001; (vi) 0.00001-0.0001; (vii) 0.000001-0.00001; (viii) 0.0000001-0.000001; (ix) <0.0000001. The second flow rate is preferably non-zero or substantially non-zero in the second mode of operation.

The liquid chromatography system preferably switches, in use, from the first mode of operation to the second mode of operation upon determining, analysing, measuring, detecting, predicting or estimating that one or more analytes of interest or one or more components are emerging, eluting or being transmitted from the first column.

The liquid chromatography system preferably switches, in use, from the second mode of operation to the first mode of operation after a predetermined time.

The predetermined time is preferably selected from the group consisting of: (i) <1 s; (ii) 1-10 s; (iii) 10-20 s; (iv) 20-30 s; (v) 30-40 s; (vi) 40-50 s; (vii) 50-60 s; (viii) 60-70 s; (ix) 70-80 s; (x) 80-90 s; (xi) 90-100 s; (xii) 100-110 s; (xiii) 110-120 s; (xiv) 120-130 s; (xv) 130-140 s; (xvi) 140-150 s; (xvii) 150-160 s; (xviii) 160-170 s; (xix) 170-180 s; (xx) 180-190 s; (xxi) 190-200 s; (xxii) 200-210 s; (xxiii) 210-220 s; (xxiv) 220-230 s; (xxv) 230-240 s; (xxvi) 240-250 s; (xxvii) 250-260 s; (xxviii) 260-270 s; (xxix) 270-280 s; (xxx) 280-290 s; (xxxi) 290-300 s; and (xxxii) >300 s.

The liquid chromatography system preferably switches, in use, from the first mode of operation to the second mode of operation in a time $t_1$, wherein $t_1$ is selected from the group consisting of: (i) $\leq 10$ s; (ii) $\leq 9$ s; (iii) $\leq 8$ s; (iv) $\leq 7$ s; (v) $\leq 6$ s; (vi) $\leq 5$ s; (vii) $\leq 4$ s; (viii) $\leq 3$ s; (ix) $\leq 2$ s; (x) $\leq 1$ s; (xi) $\leq 0.75$ s; (xii) $\leq 0.5$ s; (xiii) $\leq 0.25$ s; (xiv) $\leq 0.1$ s; and (xv) substantially instantaneously.

In the second mode of operation fluid dispensed from the first fluid delivery system A,B is preferably substantially diverted away from the first (analytical) column to waste.

In the second mode of operation preferably at least 50%, 60%, 70%, 80%, 90%, 95%, 99% or 99.9% of the first fluid A,B dispensed from the first fluid delivery system A,B is substantially not transmitted to the first (analytical) column.

In the second mode of operation preferably substantially 100% of the fluid dispensed from the first fluid delivery device A,B is diverted away from the first (analytical) column or is substantially not transmitted to the first (analytical) column.

When the liquid chromatography system switches from the first mode of operation to the second mode of operation preferably the column head pressure associated with the first (analytical) column is preferably substantially reduced or removed in a time $t_2$, wherein $t_2$ is selected from the group consisting of: (i) $\leq 10$ s; (ii) $\leq 9$ s; (iii) $\leq 8$ s; (iv) $\leq 7$ s; (v) $\leq 6$ s; (vi) $\leq 5$ s; (vii) $\leq 4$ s; (viii) $\leq 3$ s; (ix) $\leq 2$ s; (x) $\leq 1$ s; (xi) $\leq 0.75$ s; (xii) $\leq 0.5$ s; (xiii) $\leq 0.25$ s; (xiv) $\leq 0.1$ s; and (xv) substantially instantaneously.

In the first mode of operation fluid dispensed by the first fluid delivery system A,B preferably causes analyte to be passed from a second column (e.g. pre-column) to the first (analytical) column.

In the first mode of operation the first fluid delivery system A,B preferably serves to maintain a substantially constant or regular flow of fluid (e.g. solvent) through the first (analytical) column.

In the first mode of operation the first fluid (e.g. solvent) preferably passes through the first (analytical) column at a flow rate of x ml/min, and wherein in the second mode of operation the first fluid passes through the first column at a flow rate of y ml/min. Preferably, y is selected from the group consisting of: (i) $\leq 0.2$ x; (ii) 0.15-0.20 x; (iii) 0.10-0.15 x; (iv) 0.05-0.10 x; (v) 0.01-0.05 x; (vi) $\leq 0.01$ x; (vii) substantially zero; and (viii) 0.

Preferably, analyte having a specific mass to charge ratio has in the first mode of operation a peak elution time selected from the group consisting of: (i) $\leq 1$ s; (ii) 1-2 s; (iii) 2-3 s; (iv) 3-4 s; (v) 4-5 s; (vi) 5-6 s; (vii) 6-7 s; (viii) 7-8 s; (ix) 8-9 s; (x) 9-10 s; (xi) 10-15 s; (xii) 15-20 s; (xiii) 20-25 s; (xiv) 25-30 s; (xv) 30-35 s; (xvi) 35-40 s; (xvii) 40-45 s; (xviii) 45-50 s; and (xix) >50 s.

Analyte having a specific mass to charge ratio preferably has in the second mode of operation a peak elution time selected from the group consisting of: (i) <1 s; (ii) 1-10 s; (iii)

10-20 s; (iv) 20-30 s; (v) 30-40 s; (vi) 40-50 s; (vii) 50-60 s; (viii) 60-70 s; (ix) 70-80 s; (x) 80-90 s; (xi) 90-100 s; (xii) 100-110 s; (xiii) 110-120 s; (xiv) 120-130 s; (xv) 130-140 s; (xvi) 140-150 s; (xvii) 150-160 s; (xviii) 160-170 s; (xix) 170-180 s; (xx) 180-190 s; (xxi) 190-200 s; (xxii) 200-210 s; (xxiii) 210-220 s; (xxiv) 220-230 s; (xxv) 230-240 s; (xxvi) 240-250 s; (xxvii) 250-260 s; (xxviii) 260-270 s; (xxix) 270-280 s; (xxx) 280-290 s; (xxxi) 290-300 s; and (xxxii) >300 s.

The analyte having a specific mass to charge ratio preferably has a mass to charge ratio selected from the group consisting of: (i) <100; (ii) 100-200; (iii) 200-300; (iv) 300-400; (v) 400-500; (vi) 500-600; (vii) 600-700; (viii) 700-800; (ix) 800-900; (x) 900-1000; (xi) 1000-1100; (xii) 1100-1200; (xiii) 1200-1300; (xiv) 1300-1400; (xv) 1400-1500; (xvi) 1500-1600; (xvii) 1600-1700; (xviii) 1700-1800; (xix) 1800-1900; (xx) 1900-2000; and (xxi) >2000.

In a third (pre-loading) mode of operation a sample mixture comprising an analyte is preferably dispensed from the second fluid delivery device C.

In the third mode of operation the analyte is preferably held on, held by or otherwise retained by or on a second column (i.e. pre-column).

The second column (i.e. pre-column) preferably comprises a reverse phase High Performance Liquid Chromatography (HPLC) column. Less preferably, the second column (i.e. pre-column) may comprise a normal phase column.

The second column (i.e. pre-column) preferably has an internal diameter selected from the group consisting of: (i) <50 µm; (ii) 50-100 µm; (iii) 100-200 µm; (iv) 200-300 µm; (v) 300-400 µm; (vi) 400-500 µm; (vii) 500-600 µm; (viii) 600-700 µm; (ix) 700-800 µm; (x) 800-900 µm; (xi) 900-1000 µm; (xii) 1.0-1.5 mm; (xiii) 1.5-2.0 mm; (xiv) 2.0-2.5 mm; (xv) 2.5-3.0 mm; (xvi) 3.0-3.5 mm; (xvii) 3.5-4.0 mm; (xviii) 4.0-4.5 mm; (xix) 4.5-5.0 mm; (xx) 5.0-5.5 mm; (xxi) 5.5-6.0 mm; (xxii) 6.0-6.5 mm; (xxiii) 6.5-7.0 mm; (xxiv) 7.0-7.5 mm; (xxv) 7.5-8.0 mm; (xxvi) 8.0-8.5 mm; (xxvii) 8.5-9.0 mm; (xxviii) 9.0-9.5 mm; (xxix) 9.5-10.0 mm; and (xxx) >10.0 mm.

The second column (pre-column) preferably has a length selected from the group consisting of: (i) <10 mm; (ii) 10-20 mm; (iii) 20-30 mm; (iv) 30-40 mm; (v) 40-50 mm; (vi) 50-60 mm; (vii) 60-70 mm; (viii) 70-80 mm; (ix) 80-90 mm; (x) 90-100 mm; (xi) 100-110 mm; (xii) 110-120 mm; (xiii) 120-130 mm; (xiv) 130-140 mm; (xv) 140-150 mm; (xvi) 150-160 mm; (xvii) 160-170 mm; (xviii) 170-180 mm; (xix) 180-190 mm; (xx) 190-200 mm; (xxi) 200-210 mm; (xxii) 210-220 mm; (xxiii) 220-230 mm; (xxiv) 230-240 mm; (xxv) 240-250 mm; (xxvi) 250-260 mm; (xxvii) 260-270 mm; (xxviii) 270-280 mm; (xxix) 280-290 mm; (xxx) 290-300 mm; and (xxxi) >300 mm.

The second column preferably comprises C4, C8 or C18 stationary phase.

The second column preferably comprises particles having a size selected from the group consisting of: (i) <1 µm; (ii) 1-2 µm; (iii) 2-3 µm; (iv) 3-4 µm; (v) 4-5 µm; (vi) 5-6 µm; (vii) 6-7 µm; (viii) 7-8 µm; (ix) 8-9 µm; (x) 9-10 µm; (xi) 10-15 µm; (xii) 15-20 µm; (xiii) 20-25 µm; (xiv) 25-30 µm; (xv) 30-35 µm; (xvi) 35-40 µm; (xvii) 40-45 µm; (xviii) 45-50 µm; (xix) >50 µm.

The second column preferably comprises particles having a pore size selected from the group consisting of: (i) <100 angstroms; (ii) 100-200 angstroms; (iii) 200-300 angstroms; (iv) 300-400 angstroms; (v) 400-500 angstroms; (vi) 500-600 angstroms; (vii) 600-700 angstroms; (viii) 700-800 angstroms; (ix) 800-900 angstroms; (x) 900-1000 angstroms; and (xi) >1000 angstroms.

In the third (pre-loading) mode of operation salts and/or other contaminants are preferably at least partially or substantially removed from the sample mixture and exit the second column (i.e. pre-column).

In the third mode of operation the relative concentration of analyte in the sample mixture is preferably substantially increased whilst being held on, held by or otherwise retained by or on the second column.

The liquid chromatography system preferably switches to the first mode of operation after the third mode of operation.

According to another aspect of the present invention there is provided an analytical instrument comprising a liquid chromatography system as described above.

Preferably, the analytical instrument is selected from the group consisting of: (i) an ultra-violet (UV) detector; (ii) an ultra-violet (UV) array detector; (iii) an infra-red (IR) detector; (iv) an ion mobility separator; (v) an ion mobility spectrometer; (vi) a visible ultra-violet (UV) detector; (vii) a Nuclear Magnetic Resonance (NMR) detector; (viii) an Electrospray Light Scattering Detector (ELSD); (ix) a further liquid chromatography system (LC-LC); (x) a refractive index (RI) detector; (xi) a visible detector; (xii) a chemiluminescence detector; and (xiii) a fluorescence detector.

According to another aspect of the present invention there is provided a mass spectrometer comprising a liquid chromatography system as described above.

The mass spectrometer preferably further comprises an ion source coupled to the first column. The ion source may be selected from the group consisting of: (i) an Electrospray ("ESI") ion source; (ii) an Atmospheric Pressure Chemical Ionisation ("APCI") ion source; (iii) an Atmospheric Pressure Photo Ionisation ("APPI") ion source; (iv) a Laser Desorption Ionisation ("LDI") ion source; (v) an Inductively Coupled Plasma ("ICP") ion source; (vi) an Electron Impact ("EI") ion source; (vii) a Chemical Ionisation ("CI") ion source; (viii) a Field Ionisation ("FI") ion source; (ix) a Fast Atom Bombardment ("FAB") ion source; (x) a Liquid Secondary Ion Mass Spectrometry ("LSIMS") ion source; (xi) an Atmospheric Pressure Ionisation ("API") ion source; (xii) a Field Desorption ("FD") ion source; (xiii) a Matrix Assisted Laser Desorption Ionisation ("MALDI") ion source; (xiv) a Desorption/Ionisation on Silicon ("DIOS") ion source; (xv) a Desorption Electrospray Ionisation ("DESI") ion source; and (xvi) a Nickel-63 radioactive ion source.

The ion source preferably comprises a continuous or pulsed ion source.

The liquid chromatography system preferably switches from the first mode of operation to the second mode of operation upon determining that analyte ions of interest are being eluted to or emitted from the ion source.

The mass spectrometer preferably further comprises a mass analyser. The mass analyser is preferably selected from the group consisting of: (i) an orthogonal acceleration Time of Flight mass analyser; (ii) an axial acceleration Time of Flight mass analyser; (iii) a quadrupole mass analyser; (iv) a Penning mass analyser; (v) a Fourier Transform Ion Cyclotron Resonance ("FTICR") mass analyser; (vi) a 2D or linear quadrupole ion trap; (vii) a Paul or 3D quadrupole ion trap; and (viii) a magnetic sector mass analyser.

According to another aspect of the present invention there is provided a method of liquid chromatography comprising:

providing a first column, a first fluid delivery system for delivering a first fluid to the first column and a second fluid delivery system for delivering a second different fluid to the first column;

passing fluid through the first column by means of the first fluid delivery system at a first flow rate; and then substantially diverting the first fluid away from the first column and passing the second different fluid through the first column by means of the second fluid delivery system at a second different flow rate.

According to another aspect of the present invention there is provided a method of mass spectrometry comprising the method of liquid chromatography as described above.

The preferred embodiment advantageously enables an extended time to be spent analysing species or analytes of interest that elute from a liquid chromatography column thereby enabling the observed ion counts to be increased and the signal to noise ratio to be increased (or allowing more experiments to be performed when multiple components are co-eluting).

The preferred chromatography system comprises a liquid chromatograph pump with three pumping trays A,B,C. Two of the pumping trays A,B are preferably used for solvent gradient formation whilst the third C is preferably used for loading a sample and for elution at relatively lower flow rates. An advantage of the preferred chromatography system is that the preferred system does not require any restrictors to control the flow rate. Furthermore, a post-column valve is not required and is preferably not used so that the preferred system does not suffer from the detrimental effects to chromatographic performance caused by the introduction of a dead volume.

The preferred embodiment enables peak parking to be performed in an improved manner compared with other known approaches to peak parking. In particular, when the mass analyser, mass spectrometer or other analytical instrument identifies the presence of a species or analyte of interest, a pulse, signal or other indication is preferably sent to the liquid chromatography pump(s) A,B. The solvent gradient due to solvent channel A,B is then preferably halted, preferably substantially immediately, and the flow from the pump(s) A,B is preferably either reduced or substantially stopped altogether. A valve preferably switches which preferably has the effect of substantially removing (or less preferably significantly reducing) column head pressure. The valve also enables the sample flow from an auxiliary pump C operating at a lower flow rate to be directed to the column input. A low pressure build up then preferably occurs which causes the sample or analyte to pass through or elute from the analytical column at a relatively lower flow rate and effectively therefore creates a peak parking effect.

The system may switch out of a peak parking mode of operation when a further pulse, signal or other indication is received. The further pulse, signal or indication may, for example, be sent from a mass analyser, mass spectrometer or other analytical instrument. However, according to another embodiment the system may automatically switch out of a peak parking mode of operation after a set or pre-determined period of time or by or in response to one or more other predetermined criteria. When the system switches out of a peak parking mode of operation then the valve then preferably switches back to its original position. The set flow rate is then preferably resumed and the solvent gradient due to solvent channels A, B then preferably continues from where it was previously halted.

A particularly advantageous feature of the preferred embodiment is that the preferred liquid chromatography system does not suffer from pressure relaxation problems as the head pressure is preferably dissipated almost or substantially instantaneously. The column pressure is then preferably allowed to build up due to the flow rate of an auxiliary isocratic pump C operating at a relatively low flow rate. A further advantage of the preferred system is that no post-column valve is required and hence chromatographic resolution is maintained in the system.

BRIEF DESCRIPTION OF THE DRAWINGS

Various embodiments of the present invention will now be described, by way of example only, and with reference to the accompanying drawings in which.

DETAILED DESCRIPTION OF THE INVENTION

Figure 1A:
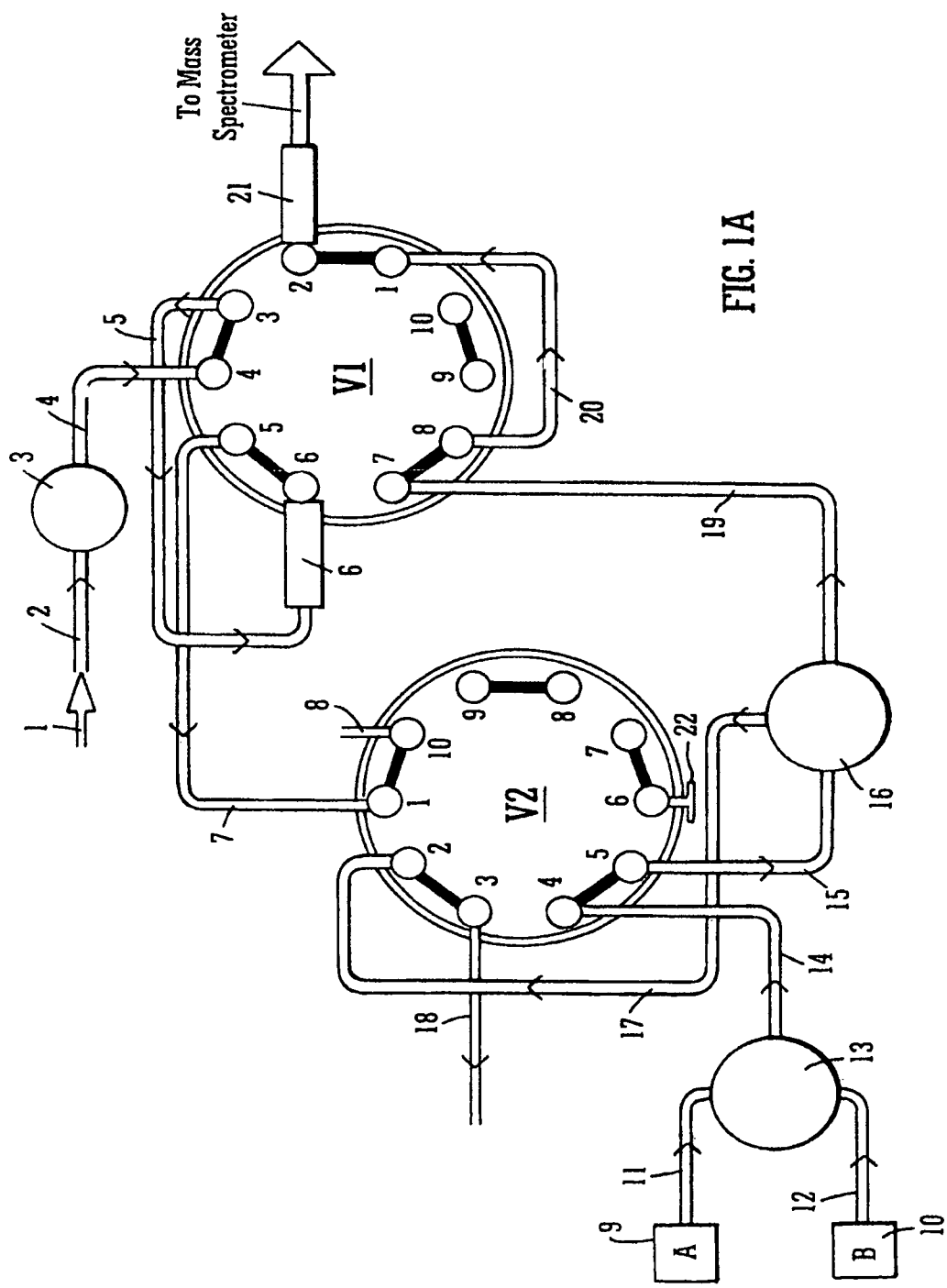
FIG. 1A shows a liquid chromatography split flow system according to a preferred embodiment during a precolumn loading mode of operation.

A preferred embodiment for implementing variable flow chromatography with a split flow chromatography system will now be described with reference to FIGS. 1A, 1B and 1C. The preferred chromatography system preferably comprises two ten-port switching valves V1, V2. Different sizes of tubing and capillaries may be used to implement the system. The valve rotor positions are indicated in each figure by thick lines. For example, with respect to valve V1 as shown in FIG. 1A, port 1 is connected to port 2, port 3 is connected to port 4, port 5 is connected to port 6, port 7 is connected to port 8, and port 9 is connected to port 10.

Figure 1B:
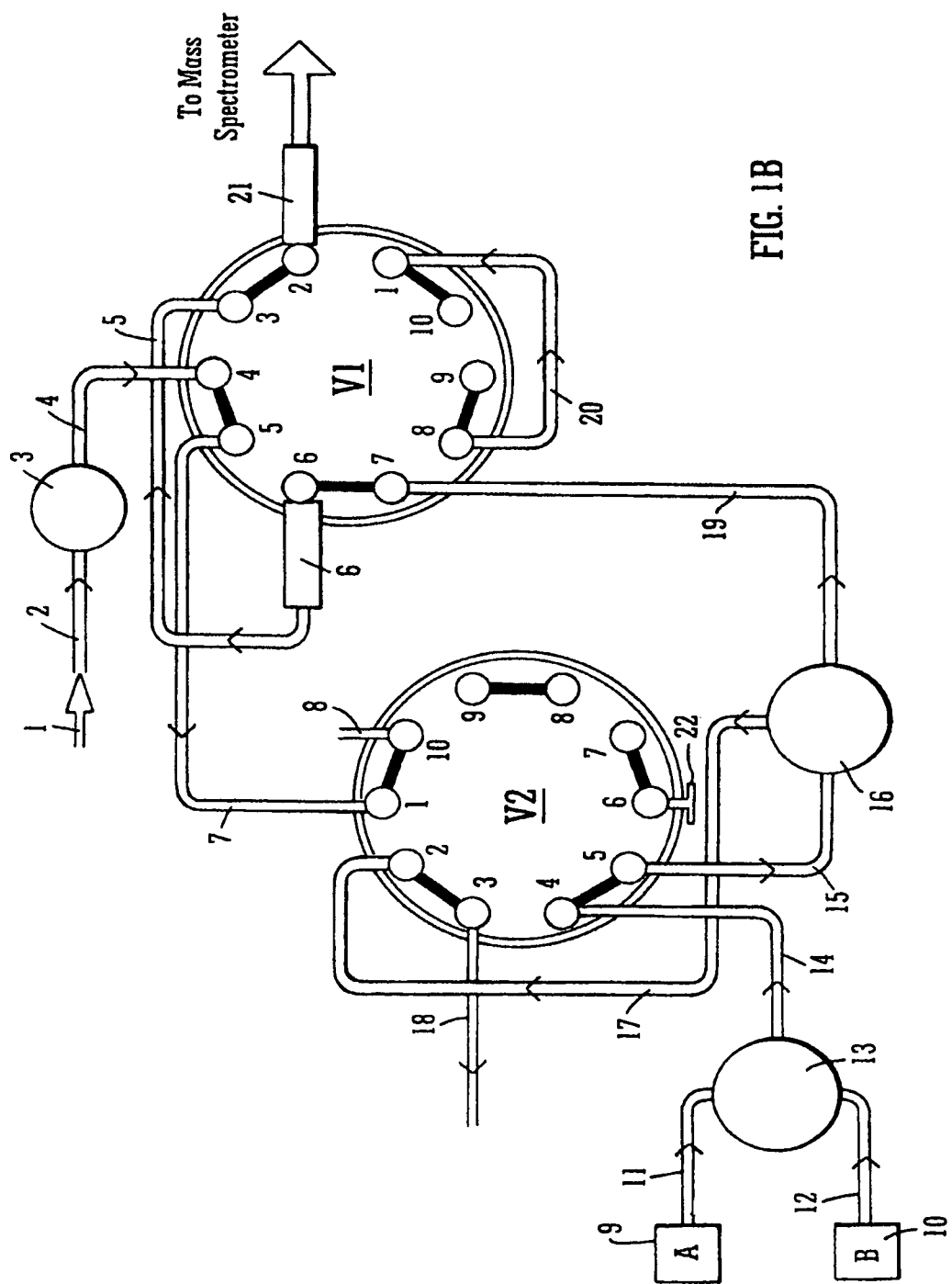
FIG. 1B shows a liquid chromatography split flow system according to a preferred embodiment during a normal flow elute mode of operation.
Figure 1C:
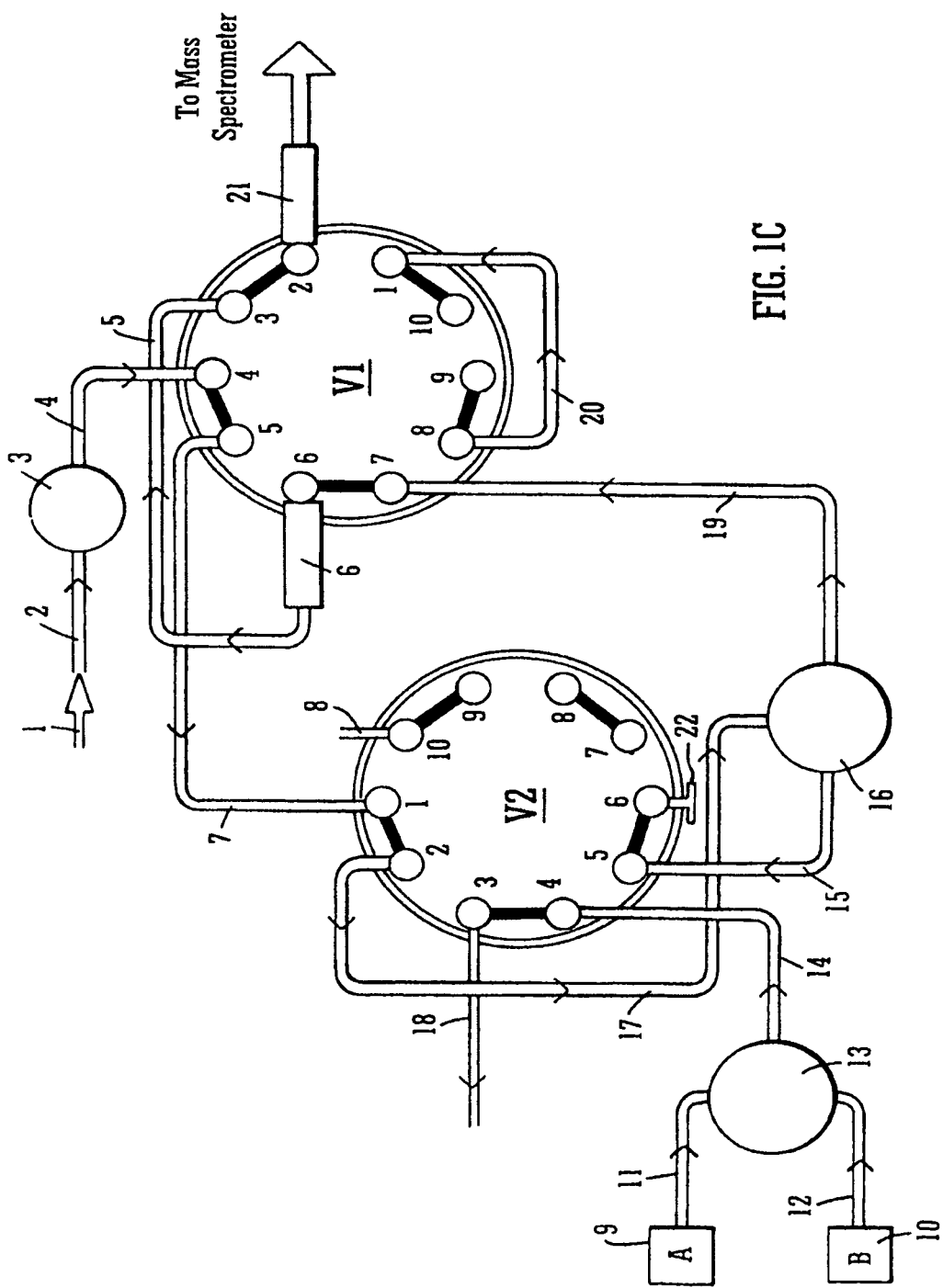
FIG. 1C shows a liquid chromatography split flow system according to a preferred embodiment during a reduced flow elute mode of operation.

The split flow chromatography system as shown in FIGS. 1A, 1B and 1C may, for example, be used in conjunction with an analytical column 21 having an inside or internal diameter of 180 μm or less. The split ratio is preferably dependent upon the back pressure of a restrictor compared with the back pressure of a precolumn 6 plus analytical column 21.

FIG. 1A shows the valve rotor positions in a precolumn loading mode of operation. A sample is preferably injected into the system at a flow rate preferably of tens of microlitres per minute via an auxiliary pump and autosampler 1. The sample then preferably passes through tubing 2, filter 3 and tubing 4 to port V1(4) of the first ten-port switching valve V1. The sample then passes to port V1(3) and leaves the valve via port V1(3) before passing through tubing 5 and becoming trapped on a precolumn 6 which is connected to port V1(6). The sample or analyte is preferably trapped on precolumn 6 whilst fluid continues to pass through the precolumn 6 to port V1(5). The fluid then leaves the valve V1 via port V1(5). The fluid then passes through tubing 7 to port V2(1) of the second ten-port switching valve V2. The fluid then passes to port V2(10) before going to waste via tubing 8.

In the precolumn loading mode of operation as shown in FIG. 1A and as described above solvent flow is meanwhile maintained through an analytical column 21 which is coupled to an ion source of a mass spectrometer. The solvent flow is maintained by two pump trays 9,10 which form part of solvent channels A,B. Liquid or solvent from the two pump trays 9,10 is preferably transferred through tubing 11,12 to a mixing T or tee-piece 13. The two solvents are then preferably mixed in the mixing T or tee-piece and the resulting mixed solvent then preferably passes through tubing 14 to valve port V2(4) and on to port V2(5). The mixed solvent then passes through tubing 15 to a splitting T or tee-piece 16. A restrictor arm of the splitting T or tee-piece 16 goes via tubing 17 to port V2(2). Fluid flows from port V2(2) to port V2(3) and then passes to a restrictor 18 before finally going to waste. Analytical flow, however, passes from the splitting T or tee-piece 16 and goes via tubing 19 to port V1(7) of the first ten-port switching valve V1. The analytical flow then passes from port V1(7) to port V1(8) before passing through tubing 20 and on to port V1(1). The analytical flow then passes from port V1(11) to port V1(2) before passing on to the analytical column 21.

The analytical column 21 is preferably coupled to a nanoflow spray device such as an Electrospray Ionisation ion source or another ion source which is preferably arranged to operate optimally at such relatively low flow rates. At least some of the resulting analyte ions produced by the spray device or ion source then preferably pass to the main body of a mass spectrometer (or less preferably to another form of analytical instrument) for subsequent mass analysis (or more generally analysis).

In the precolumn loading mode of operation as described above in relation to FIG. 1A, a plug 22 connected to port V2(6) is not used in the particular mode of operation. However, the plug 22 is used in a reduced flow elute mode of operation as will be discussed in more detail below in relation to FIG. 1C.

After a loading/desalting period has occurred wherein salts or other contaminants are removed from the sample being held on pre-column 6, valve V1 is then preferably arranged to switch from the precolumn loading mode of operation as shown in FIG. 1A to a normal flow elute mode of operation as shown in FIG. 1B and as will be discussed in more detail below.

FIG. 1B shows the preferred split flow chromatography system in a normal flow elute mode of operation. Fluid is arranged to flow at, for example, a rate of 0.4 microlitres per minute from auxiliary pump and autosampler 1. The fluid passes via tubing 2 to filter 3. After passing through the filter 3, the fluid then passes via tubing 4 to port V1(4) of the first ten-port switching valve V1. The fluid then passes from port V1(4) to port V1(5) and then passes via tubing 7 to port V2(1). The fluid then passes from port V2(1) to port V2(10) before passing via tubing 8 to waste. In this mode, there is a very low back pressure in the flow path described above.

A liquid chromatography solvent gradient is preferably performed or maintained during the normal flow elute mode of operation and is preferably arranged to flow through precolumn 6 before flowing through the analytical column 21 in the following manner. Liquid or solvent from the two pump trays 9,10 of solvent channels A,B is preferably transferred through tubing 11,12 to the mixing T to tee-piece 13. The resulting mixed solvent then preferably passes through tubing 14 to valve port V2(4) before passing on to port V2(5). The mixed solvent then preferably passes from port V2(5) out through tubing 15 to the splitting T or tee-piece 16. The restrictor arm of the split goes via tubing 17 to port V2(2). Fluid then passes from port V2(2) to port V2(3) before passing through the restrictor 18 and on to waste. The analytical flow, however, passes via tubing 19 to port V1(7). The mixed solvent then passes on to port V1(6). The analytical flow or mixed solvent then passes from port V1(6) through the precolumn 6 and then on through tubing 5 to port V1(3). The analytical flow comprising solvent mixture and any analyte released from the precolumn then passes from port V1(3) to port V1(2) and then on to the analytical column 21. The analytical column 21 is preferably coupled to a nanoflow spray device such as an Electrospray Ionisation ion source or other ion source which is preferably arranged to operate optimally at such relatively low flow rates. At least some of the resulting analyte ions are then preferably passed into a mass spectrometer for subsequent mass analysis.

In the normal flow elute mode of operation as described above, tubing 20 which interconnects valve ports V1(1) and V1(8) is not used and likewise plug 22 connected to port V2(6) is also not used.

When a species of interest or analyte of interest is detected by the mass spectrometer, mass analyser or other analytical instrument a pulse, signal or other indication is preferably sent to the pumps A,B and the system then preferably switches to a reduced flow elute mode of operation as will be described in more detail with reference to FIG. 1C.

FIG. 1C shows the preferred split flow chromatography system in a reduced flow elute mode of operation. In the reduced flow elute mode of operation valve V2 has switched from the position it was in when in the normal flow elute mode of operation as described above with reference to FIG. 1B. The switching of the valve V2 has the effect of effectively removing the back pressure to the precolumn 6 and analytical column 21. The flow rate from the two pumps 9,10 of solvent channels A,B may be reduced in accordance with a programmable split ratio or the solvent gradient may be halted or stopped at or certain solvent concentration. The effective solvent flow rate is therefore effectively reduced. The solvent from the two solvent channels A,B preferably passes via tubing 11,12 to the mixing T or tee-piece 13. The mixed solvent then preferably passes via tubing 14 to port V2(4) of the second ten-port switching valve V2. The mixed solvent then preferably passes from port V2(4) to port V2(3) before passing to the restrictor 18 and preferably going to waste.

In this mode of operation the flow from the auxiliary pump and autosampler 1 now preferably serves to produce a reduced flow through the precolumn 6 and analytical column 21 as will now be described. Fluid flow passes through tubing 2 to filter 3. The fluid then passes via tubing 4 to port V1(4). The fluid then flows from port V1(4) to port V1(5). The fluid then preferably flows through tubing 7 to port V2(1). The fluid then preferably passes from port V2(1) to port V2(2) and then via tubing 17 to split T or tee-piece 16. The arm with tubing 15 is preferably connected to port V2(5) and is preferably dead ended by a plug 22 in port V2(6). As a result, there is a slow build up of pressure. The fluid will continue to pass through tubing 19 to port V1(7). The fluid then passes to port V1(6) and on to precolumn 6. Any analyte eluting from precolumn 6 preferably continues to elute and is passed by the solvent flow through tubing 5 to port V1(3). The analyte and solvent then pass to port V1(2) and on to the analytical column 21. This causes any eluting species to exhibit longer effective elution times.

In the reduced flow elute mode of operation the fluid provided by the third pump and introduced into tubing 2 preferably comprises an aqueous solution or solvent (preferably with 1% formic acid). The aqueous solution or solvent is preferably substantially similar if not identical to the aqueous solution or solvent which is preferably dispensed from solvent channel A. In this mode of operation the system is therefore effectively being temporarily switched so that a solvent passes through precolumn 6 which is approximately equivalent to that used at the start of the solvent gradient process. Accordingly, in this mode of operation the progression of the liquid chromatography separation is preferably temporarily stopped or otherwise halted.

In the reduced flow elute mode of operation as described above tubing 8 and tubing 20 are preferably not used.

After a predetermined, preferably programmable, time period the chromatography system preferably switches back from the reduced flow elute mode of operation to the normal flow elute mode of operation as described above with reference to FIG. 1B.

An alternative direct flow embodiment will now be described with reference to FIGS. 2A, 2B and 2C. Direct flow mode is typically applicable for use with analytical columns 21 having an inside or internal diameter greater than or equal to 320 µm.

Figure 2A:
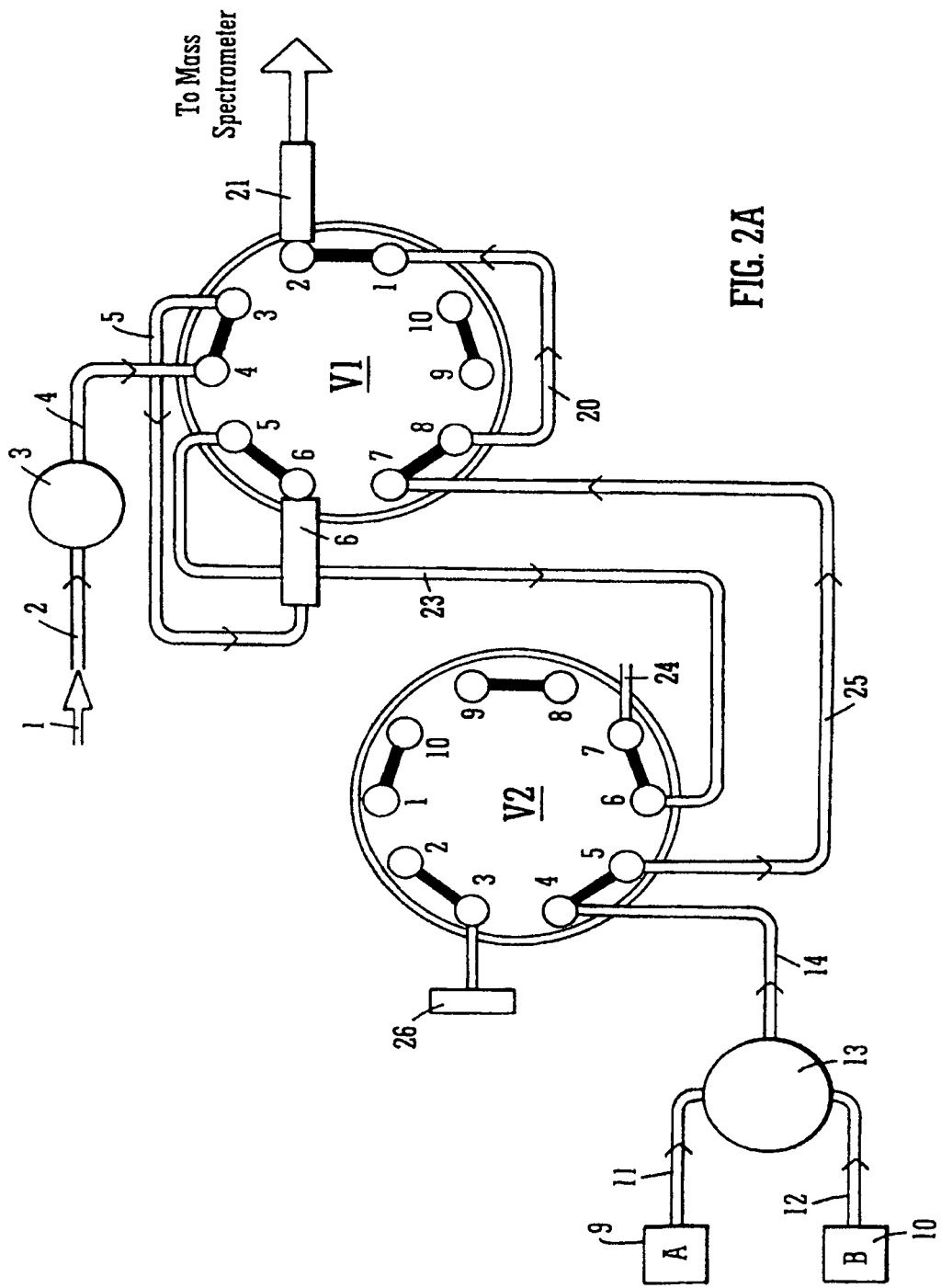
FIG. 2A shows a liquid chromatography direct flow system according to a preferred embodiment during a precolumn loading mode of operation.

FIG. 2A shows the preferred direct flow chromatography system valve rotor positions in a precolumn loading mode of operation. Sample is preferably injected into the system at a flow rate of preferably tens of microlitres per minute via an auxiliary pump and autosampler 1. The sample passes through tubing 2 and on to filter 3. The sample then passes via tubing 4 to port V1(4) of the first ten-port switching valve. The sample then passes from port V1(4) to port V1(3) before passing through tubing S. The sample then becomes trapped on the precolumn 6. Fluid will continue to pass through precolumn 6 to port V1(6). The fluid will then pass to port V1(5). The fluid is then transferred through tubing 23 to port V2(6). The fluid then passes to port V2(7) before preferably going to waste via tubing 24.

In this mode of operation, solvent flow is preferably maintained through the analytical column 21 in the following manner. Liquid from the two pump trays 9,10 of solvent channels A,B is preferably transferred through tubing 11,12 to a mixing T or tee-piece 13. The solvents are mixed in mixing T or tee-piece 13 and the mixed solvent then preferably passes through tubing 14 to valve port V2(4). The mixed solvent then preferably passes to port V2(5) before passing through tubing 25 to port V1(7). The mixed solvent then preferably passes to port V1(8) and passes via tubing 20 to port V1(1). Finally, the mixed solvent then preferably passes from port V1(1) to port V1(2) before passing to the analytical column 21. The analytical column 21 may be coupled to a nanoflow spray device such as an Electrospray Ionisation ion source or another ion source which may be arranged to operate at relatively higher flow rates. At least some of the resulting analyte ions produced by the spray device or ion source then preferably pass to the main body of a mass spectrometer (or less preferably other form of analytical instrument) for subsequent mass analysis (or more generally analysis).

In the precolumn loading mode of operation as described plug 26 is preferably not used.

Figure 2B:
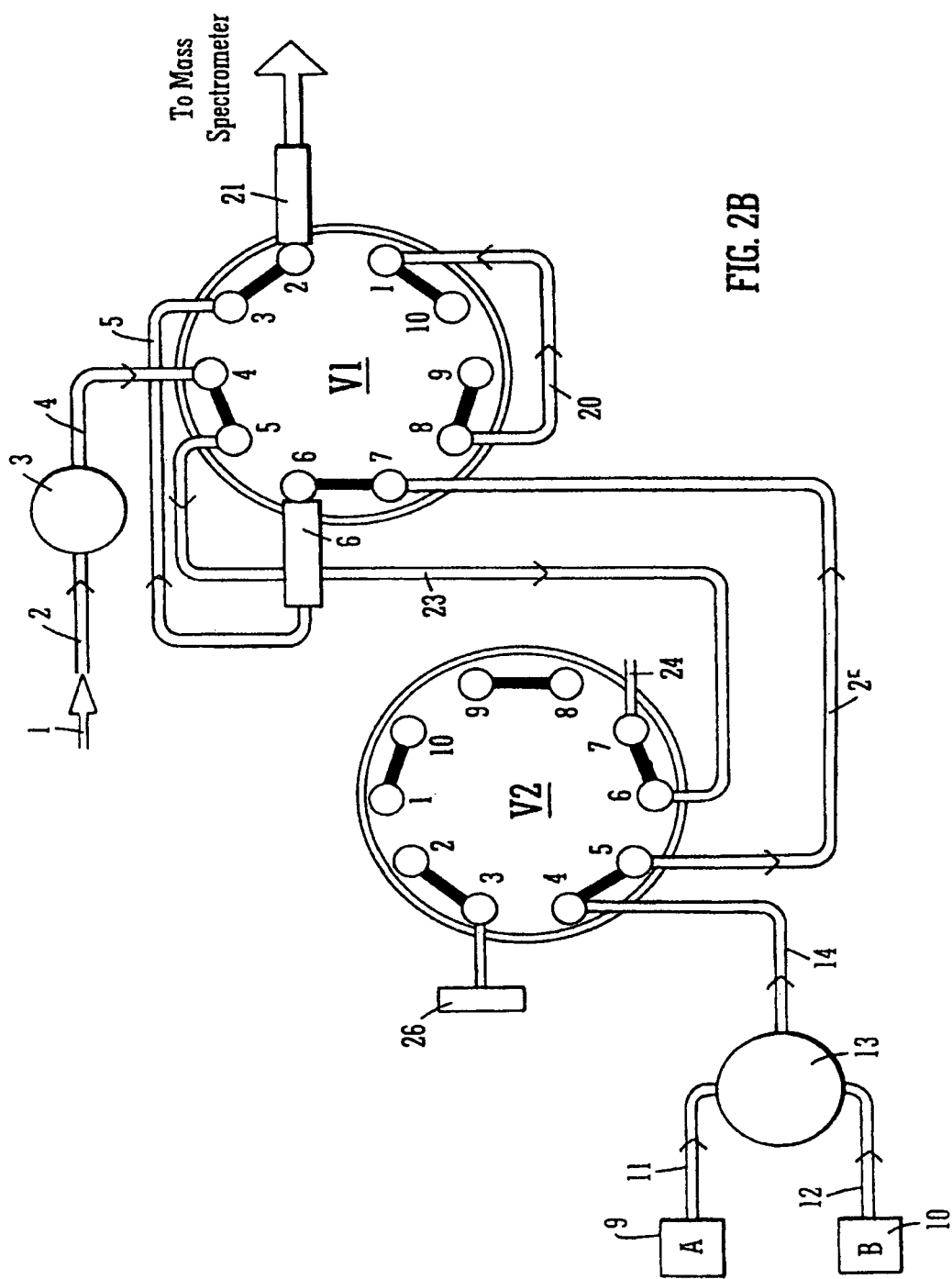
FIG. 2B shows a liquid chromatography direct flow system according to a preferred embodiment during a normal flow elute mode of operation.

After a loading/desalting period has occurred wherein salts and/or contaminants are preferably removed from the sample held on precolumn 6, the valve V1 is then preferably arranged to switch from the precolumn loading mode of operation as shown in FIG. 2A to a normal flow elute mode of operation as shown in FIG. 2B and as will be discussed in more detail below.

FIG. 2B shows the preferred direct flow chromatography system in a normal flow elude mode of operation. Fluid is preferably arranged to flow at, for example, a rate of 0.4 microlitres per minute from auxiliary pump and autosampler 1. The fluid then preferably passes via tubing 2 to filter 3. The fluid then preferably passes via tubing 4 to port V1(4) of the first ten-port switching valve V1. The fluid then preferably passes to port V1(5) and passes via tubing 23 to port V2(6).

The fluid then preferably passes from port V2(6) to port V2(7) and preferably passes via tubing 24 to waste. In this mode, there is a very low back pressure in the flow path described above.

A liquid chromatography solvent gradient is preferably performed and maintained during the normal flow elute mode of operation and is preferably arranged to flow through precolumn 6 before flowing through the analytical column 21 in the following manner. Liquid or solvent from the two pump trays 9,10 of solvent channels A,B are preferably transferred through tubing 11,12 to the mixing T or tee-piece 13. The solvents are then preferably mixed in mixing T or tee-piece 13 and the mixed solvent then preferably passes through tubing 14 to valve port V2(4) before passing on to port V2(5). The mixed solvent then preferably passes from port V2(5) via tubing 25 to port V1(7). The mixed solvent then preferably passes from port V1(7) on to port V1(6). The mixed solvent then preferably passes through precolumn 6. Any analyte eluting from precolumn 6 preferably flows with the solvent through tubing 5 to port V1(3). The solvent and an released analyte then preferably passes to valve V1(2) before preferably passing through the analytical column 21.

The analytical column 21 is preferably coupled to a nanoflow spray device such as an Electrospray Ionisation ion source or another ion source arranged to operate optimally at relatively higher flow rates. At least some of the resulting analyte ions produced by the spray device or ion source then preferably pass to the main body of a mass spectrometer (or less preferably other form of analytical instrument) for subsequent mass analysis (or more generally analysis). In the normal elute mode of operation as described above in relation to FIG. 2B tubing 20 and plug 26 are not used.

When a species of interest or analyte of interest is detected by the mass spectrometer, mass analyser or other analytical instrument a pulse, signal or other indication is preferably sent to the pumps 9,10 of the solvent channel A,B and the system then preferably switches to a reduced flow elute mode of operation as will be described in more detail with reference to FIG. 2C.

Figure 2C:
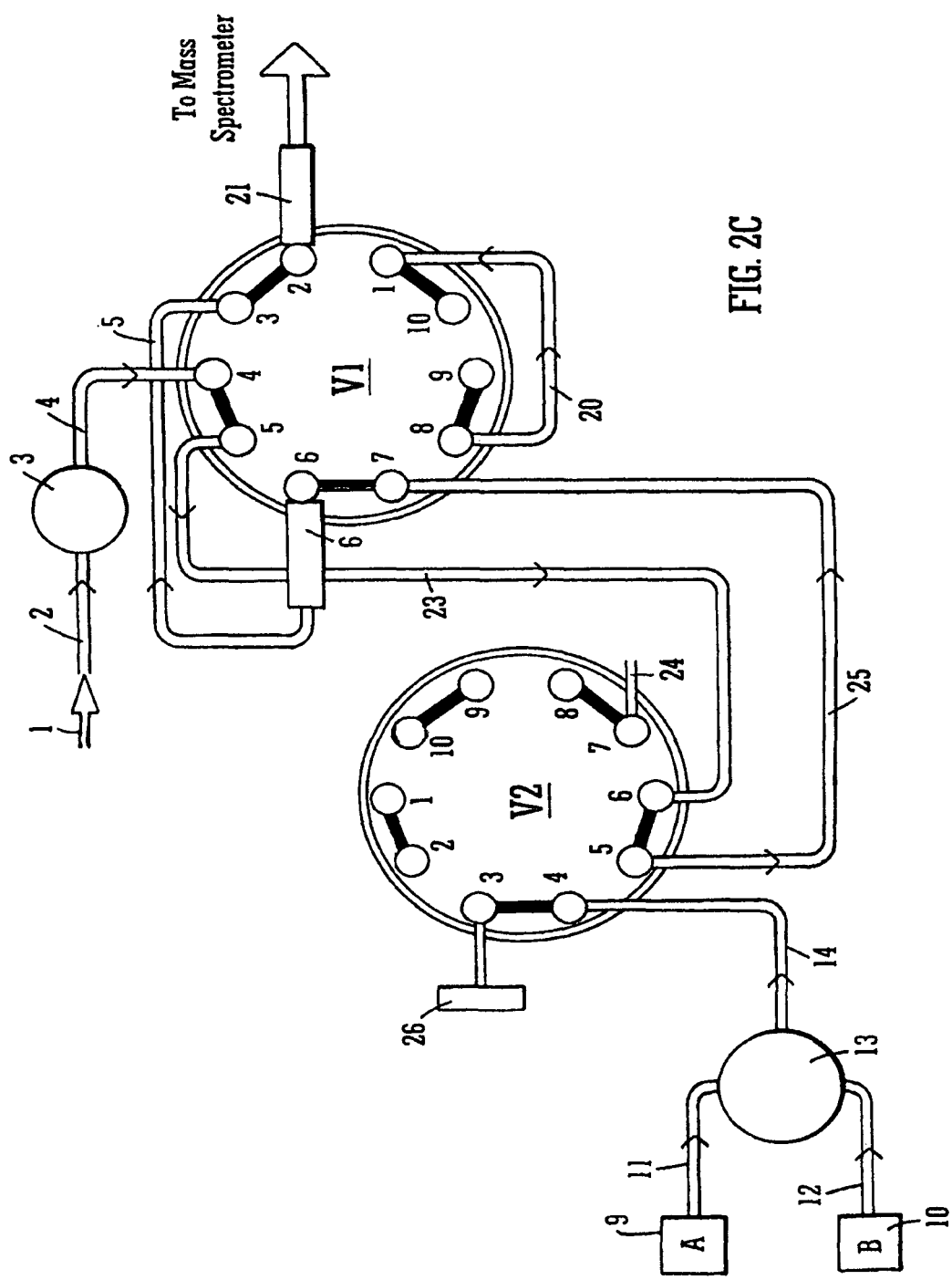
FIG. 2C shows a liquid chromatography direct flow system according to a preferred embodiment during a reduced flow elute mode of operation.

FIG. 2C shows the preferred direct flow chromatography system in a reduced flow elute mode of operation. In the reduced flow elute mode of operation valve V2 has preferably switched from the position in which it was in when in the normal flow elute mode of operation as described with reference to FIG. 2B. The switching of the valve V2 effectively removes the back pressure to the precolumn 6 and analytical column 21. The flow rate from the two pumps 9,10 of the solvent channels A,B is effectively stopped and the liquid chromatography gradient is effectively halted or stopped at the current composition or solvent gradient. Solvent from pumps 9,10 passes via tubing 11,12 to mixing T or tee-piece 13. The solvent is mixed in the mixing T or tee-piece 13 and the mixed solvent then passes via tubing 14 to port V2(4). The mixed solvent then passes to port V2(3) which in this mode of operation is connected to plug 26. The flow rate is then preferably stopped to maintain pressure at the pump heads.

The flow from the auxiliary pump connected to tubing 2 now preferably serves to produce a reduced solvent flow through precolumn 6 and analytical column 21 as will now be described. Aqueous solvent preferably flows through tubing 2 to filter 3. The fluid then preferably passes via tubing 4 to port V1(4). The fluid then preferably flows from port V1(4) to port V1(5). The fluid then passes via tubing 23 to port V2(6). The fluid then flows to port V2(5). The fluid then flows via tubing 25 to port V1(7). The fluid then passes to port V1(6) and on to precolumn 6. Any analyte eluting from precolumn 6 then preferably continues to elute and is passed by the solvent flow through tubing 5 to port V1(3). The solvent and any eluting analyte then preferably passes to port V1(2) and on to the analytical column 21. This causes any eluting species to effectively exhibit longer elution times.

In the reduced flow elute mode of operation the fluid provided by the third pump to tubing 2 preferably comprises an aqueous solution or solvent (preferably with 1% formic acid). The aqueous solution or solvent is preferably substantially similar if not identical to the aqueous solution or solvent dispensed by or from solvent channel A. In this mode of operation the system is therefore temporarily switched to use a solvent which is approximately equivalent to that used at the start of the solvent gradient process. Accordingly, in this mode of operation the progression of the liquid chromatography separation is effectively temporarily stopped or otherwise halted.

In the reduced flow elute mode of operation as described above, tubing 20 and tubing 24 are preferably not used.

After a predetermined, preferably programmable, time period the chromatography system preferably switches back from the reduced flow elute mode of operation to the normal flow elute mode of operation as described above with reference to FIG. 2B.

Figure 3:
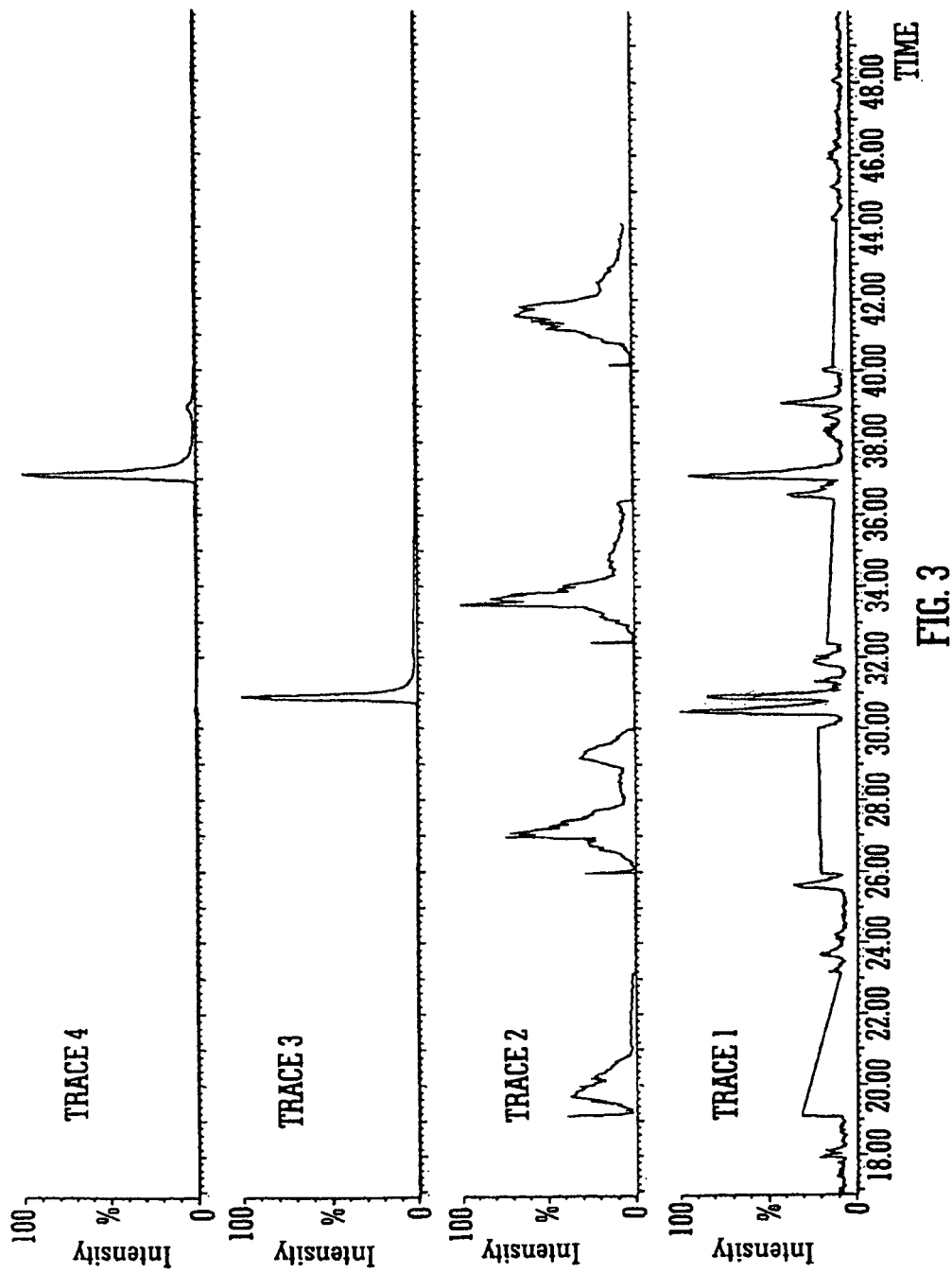
FIG. 3 shows example data obtained using a split flow liquid chromatography system as shown in FIGS. 1A-1C.

FIG. 3 shows chromatograms which resulted from the injection of 200 fmol of BSA digest onto a column having an internal diameter of 75 µm which formed part of a Waters CapLC (RTM) HPLC system operating in a split flow mode.

Figure 4:
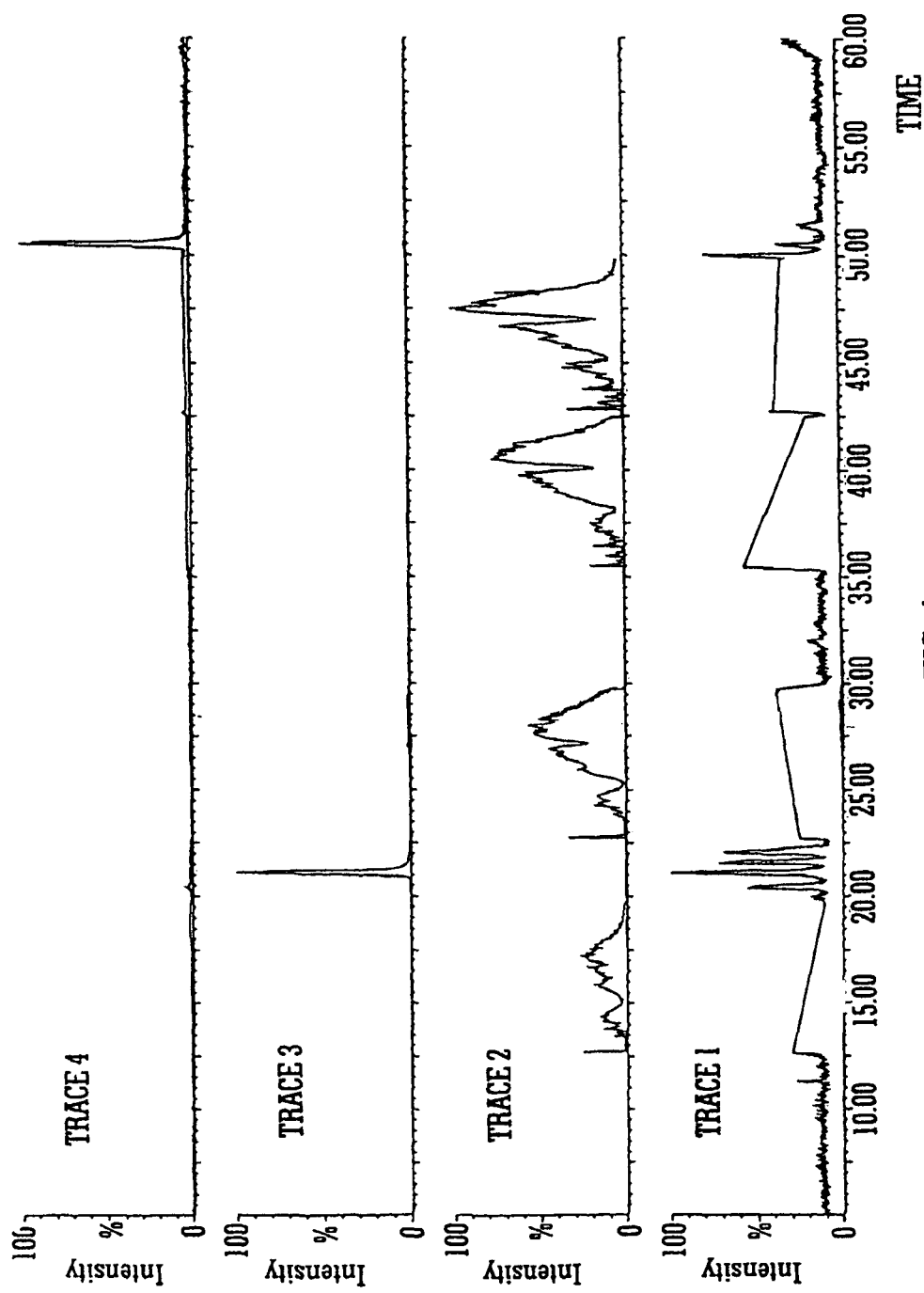
FIG. 4 shows example data obtained using a direct flow liquid chromatography system as shown in FIGS. 2A-2C.

FIG. 4 similarly shows chromatograms which resulted from the injection of 500 fmol of BSA digest onto a column having an internal diameter of 180 µm which formed part of a Waters CapLC (RTM) HPLC system operating in a direct flow mode.

In both cases a Data Dependent Acquisition (DDA) experiment was set up such that four ions were chosen for MS/MS. Trace 1 of FIGS. 3 and 4 shows the TIC and is the MS Base Peak. Trace 2 of FIGS. 3 and 4 shows the TIC and is the MS/MS Base Peak. The collision energy in the MS/MS mode was kept relatively low to preserve the parent ion in the MS/MS mode. Traces 3 and 4 of FIGS. 3 and 4 are ions in a MS mode that had not been chosen for MS/MS.

The data shows that a significant peak parking effect is achieved in a MS/MS mode of operation and that chromatographic resolution is also well maintained for ions that are not chosen for MS/MS.

Further embodiments are contemplated (not shown) wherein different connection arrangements on valve V1 are used to allow the flow from an auxiliary pump C to be diverted through a restrictor in the normal flow elute mode. This has the effect of raising or increasing the back pressure which reduces the pressure shock seen by the pump when entering a reduced flow elute mode of operation.

The stream select valves V1,V2 may according to alternative less preferred embodiments comprise valves having an alternative number of ports. For example, the valves V1,V2 may comprise six, seven, eight, nine or more than ten ports.

It is also contemplated that the flow of the effective isocratic pump due to pumps 9,10 in normal flow elute mode of operation and the auxiliary pumps in a reduced flow elute mode of operation may be varied in different experiments in order to alter the peak elution profiles.

Whilst the preferred and less preferred embodiments have been described in relation to a liquid chromatography system, it is also contemplated that the disclosed chromatography system could be used as part of a gas chromatography system.

Although the present invention has been described with reference to preferred embodiments, it will be understood by those skilled in the art that various changes in form and detail may be made without departing from the scope of the invention as set forth in the accompanying claims.

The invention claimed is:

1. A method of chemical separation, comprising:
dispensing a sample from a sample pumping system;
pumping a first solvent from a solvent gradient pumping system to elute the dispensed sample through a separation column;
identifying an analyte of interest in the eluting sample; and
pumping a second solvent from the sample pumping system at a reduced flow rate to peak-park the analyte in the separation column.

2. The method of claim 1, wherein dispensing comprises loading the sample onto a trap column.

3. The method of claim 2, further comprising removing one or more contaminants from the sample loaded onto the trap column.

4. The method of claim 1, wherein identifying comprises determining, analyzing, measuring, detecting, predicting or estimating that the analyte is emerging, eluting or being transmitted from the separation column.

5. The method of claim 1, wherein the solvent gradient pumping system comprises two pumps.

6. The method of claim 5, wherein the two pumps comprise piston pumps.

7. The method of claim 5, wherein the solvent gradient pumping system further comprises an aqueous solvent source.

8. The method of claim 5, wherein the solvent gradient pumping system further comprises an organic solvent source.

9. The method of claim 8, wherein the organic solvent source comprises acetonitrile.

10. The method of claim 1, wherein pumping the first solvent from the solvent gradient pumping system comprises providing an isocratic flow of the first solvent.

11. The method of claim 1, wherein the sample pumping system comprises a syringe pump.

12. The method of claim 1, wherein the sample pumping system comprises a peristaltic pump.

13. The method of claim 1, wherein pumping the second solvent from the sample pumping system provides an isocratic flow of the second solvent.

14. The method of claim 1, wherein pumping the first solvent from the solvent gradient pumping system comprises providing a flow rate in a range of 400 nl/min to 500 nl/min.

15. The method of claim 1, wherein the reduced flow rate is in a range of 40 nl/min to 50 nl/min.

16. The method of claim 1, wherein a ratio of the reduced flow rate to a flow rate of the solvent gradient pumping system is in a range of 0.01 to 0.1.

17. The method of claim 1, wherein the separation column comprises a reverse-phase column.

18. The method of claim 1, wherein pumping the second solvent from the sample pumping system comprises diverting the first solvent away from the separation column.

19. The method of claim 1, wherein pumping the second solvent from the sample pumping system comprises substantially reducing or removing a head pressure associated with the separation column in a time selected from the group consisting of: (i) <10 s; (ii) <9 s; (iii) <8 s; (iv) <7 s; (v) <6 s; (vi) <5 s; (vii) <4 s; (viii) <3 s; (ix) <2 s; (x) <1 s; (xi) <0.75 s; (xii) <0.5 s; (xiii) <0.25 s; (xiv) <0.1 s; and (xv) substantially instantaneously.

20. The method of claim 1, wherein identifying the analyte of interest comprises observing the eluting sample with a detector selected from the group consisting of: (i) an ultra-violet (UV) detector; (ii) an ultra-violet (UV) array detector;

(iii) an infra-red (IR) detector; (iv) an ion mobility separator; (v) an ion mobility spectrometer; (vi) a visible ultra-violet (UV) detector; (vii) a Nuclear Magnetic Resonance (NMR) detector; (viii) an Electrospray Light Scattering Detector (ELSD); (ix) a further liquid chromatography system (LC-LC); (x) a refractive index (RI) detector; (xi) a visible or; (xii) a chemiluminescence detector; (xiii) a fluorescence detector; and (xiv) a mass-analyzer detector.

* * * * *